United States Patent [19]
Sibalis

[11] Patent Number: 5,088,977
[45] Date of Patent: Feb. 18, 1992

[54] ELECTRICAL TRANSDERMAL DRUG APPLICATOR WITH COUNTERACTOR AND METHOD OF DRUG DELIVERY

[75] Inventor: Dan Sibalis, Stony Brook, N.Y.

[73] Assignee: Drug Delivery Systems Inc., New York, N.Y.

[21] Appl. No.: 287,348

[22] Filed: Dec. 21, 1988

[51] Int. Cl.⁵ .................................. A61N 1/30
[52] U.S. Cl. ...................... 604/20; 604/892.1; 128/783
[58] Field of Search .................... 604/20-21, 604/890.1, 892.1, 896.1, 897.1; 128/783, 798-799, 803

[56] References Cited

U.S. PATENT DOCUMENTS

| | | | |
|---|---|---|---|
| 3,742,951 | 7/1973 | Zaffaroni | 604/897 |
| 4,449,983 | 5/1984 | Cortese et al. | 604/892.1 |
| 4,460,372 | 7/1984 | Campbell et al. | 604/897 |
| 4,708,716 | 11/1987 | Sibalis | 128/635 X |
| 4,731,049 | 3/1988 | Parsi | 604/20 |
| 4,734,090 | 3/1988 | Sibalis | 604/20 |

*Primary Examiner*—Lee S. Cohen
*Assistant Examiner*—J. P. Lacyk
*Attorney, Agent, or Firm*—Lackenbach Siegel Marzullo & Aronson

[57] ABSTRACT

An electrical transdermal drug applicator provides enhanced drug flow to the bloodstream of the subject by delivering a primary drug into a subject's circulatory system for therapeutic purposes, and delivering from the same or other reservoir a non-therapeutic counteracting agent to the skin of the patient which induces flow enhancement and allows delivery of the primary drug systemically over a longer period of time and in greater quantity than heretofore appeared possible using electric current.

7 Claims, 3 Drawing Sheets

FIG. 1

ELECTRICAL TRANSDERMAL DRUG APPLICATOR WITH COUNTERACTOR AND METHOD OF DRUG DELIVERY

BACKGROUND OF THE INVENTION

This invention relates generally to an electrical transdermal drug device delivering a drug to the patient for systemic distribution by blood flow using principles of electrokinetic phenomena, such as electrophoresis and electroosmosis, and more particularly to an electrical transdermal drug applicator or patch delivering counteracting substances locally to the patient's skin and/or electrically inducing the skin to produce endogenous compounds which extend the period of therapeutic drug delivery and thereby increase usefulness of the drug applicator. Reference to or disclosure of devices for transdermal delivery of drugs by application of electrical current through the skin of a person or animal are shown in the following U.S. Pat.:

| | |
|---|---|
| 385,556 | 4,243,052 |
| 486,902 | 4,325,367 |
| 588,479 | 4,367,745 |
| 2,493,155 | 4,419,019 |
| 2,267,162 | 4,474,570 |
| 2,784,715 | 4,406,658 |
| 3,163,166 | 4,314,554 |
| 3,289,671 | 4,166,457 |
| 3,547,107 | 4,239,052 |
| 3,677,268 | 4,290,878 |
| 4,008,721 | 4,164,226 |
| 4,141,359 | 4,362,645 |
| 4,239,046 | 4,273,135 |

The following foreign patents refer to or disclose transdermal drug delivery devices:
EPA No. 0060452
DE No. 290202183
DE No. 3225748
EPA No. 0058920
UK No. 2104388

Thus, it is evident, that transdermal delivery of drugs by application of an electrical current is not unknown. Yet, except for experimental and developmental purposes, such electrical transdermal drug applicators are not presently commercially available for use by medical professionals or by individuals.

A problem with transdermal patches, especially electrically powered patches, is that such devices exhibit a rate of drug delivery which decays with passage of time despite a steady state condition for the applied electrical current and steady state drug concentrations within the drug reservoir of the device. This phenomenon has been reported in scientific journals, for example, an article, IN VIVO TRANSDERMAL DELIVERY OF INSULIN, Chien et al, Annals of New York Academy of Sciences, pages 38–47 (1987).

Therein, changes in blood glucose level are recorded versus time after insulin is delivered transdermally to laboratory animals, using an electrical current. Several parameters are varied. For example, it is reported that a pulsed DC current has a greater and more enduring effect in reducing blood glucose levels in laboratory animals, than does a pure continuous DC current. The actual quantity of insulin, which is delivered, is not measured. Rather, the effect of the drug in reducing blood glucose levels is measured. It is found that one repetition rate of DC pulses is more effective than another pulse repetition rate in reducing blood glucose levels measured both in magnitude and time duration. A square waveform provided better results than did a sinusoidal waveform or a trapezoidal waveform.

The authors of the paper analogize the skin electrically with resistances and capacitance in parallel as an equivalent circuit. They theorize that the DC current charges the capacitance of the skin which, once charged, can accept no more current and accordingly limits drug delivery. Using DC pulses rather than steady state current allows time for the skin capacitance to discharge, such that on the next pulse, additional current, capacitor charging, and drug delivery can occur.

However, an anomalous situation arises when at a favorable pulse repetition rate, and with the same current delivery level as in prior tests, the duty cycle is varied. It would be expected that the greater the duty cycle, that is, the greater the current ON time versus the current OFF time ratio, the greater amount of insulin would be delivered transdermally and the measured effects on blood glucose level would be correspondingly more favorable and more enduring. Contrary to expectations, as the duty cycle increases from a one-to-one ratio toward an eight-to-one ratio, the reduction in blood glucose level becomes less, rather than more, although duration of this reduction is somewhat extended.

In summary, application of current over a longer period of time, that is, consumption of more energy for delivering drugs transdermally, results in what appears to be less delivery of drug as measured by the effect on blood glucose level.

That publication graphically illustrates the problem with prior art transdermal drug applicators and delivery methods using electrical current to carry drugs through the skin, that is, the effectiveness of the delivered drug is insufficient in duration of effect and the rate of drug delivery falls off as the delivering current is continuously applied over extended periods of time.

What is needed is an electrical transdermal drug applicator and method which provide enhanced drug delivery to the patient with regard to quantity of systemically delivered drug and duration of drug effectiveness.

SUMMARY OF THE INVENTION

Generally speaking, in accordance with the invention, an electrical transdermal drug applicator having enhanced drug flow to the bloodstream of the subject is provided. The applicator, in addition to delivering a primary drug into a subject's circulatory system for therapeutic purposes, delivers from a reservoir a nontherapeutic counteracting agent to the skin of the patient which induces flow enhancement and allows delivery of the primary drug systemically over a longer period of time and in greater quantity than heretofore appeared possible using electrolytic current. Construction of the electrical transdermal drug applicator with electrochemical flow enhancement by introduction of a counteracting agent to the skin and/or specific electrical wave shapes is based on applicant's appraisal of known phenomena as described above.

However, charging of skin capacitance is not considered to be the primary factor in reducing drug delivery capability as current application time and magnitude of current are increased. The efficiency of administration of insulin may be partially vitiated by adsorption and degradation within the skin tissues or by restricted blood circulation in the skin. The passage of current and/or dissociated water ions and/or certain drugs through the human skin causes a series of events related to reduction in magnitude of negative net surface charge exhibited by living mammalian cells. A most important consequence of reduction in magnitude of the negative charge on the cells is triggering of an avalanche-like coagulation process which forms thrombi, that is, blood clotting, which in turn stops blood flow through capillaries. Passage of current from a transdermal applicator tends to reduce the negative charge on cells of the skin proximate the applicator reservoir, where drugs are delivered, causing blood clotting in the capillaries which not only stops local blood flow, but also stops drug flow into the circulatory system of the subject. A drug transdermally delivered locally is not effective systemically when the capillaries of the skin contain coagulated blood.

In addition, especially in the anodic (+) region of current delivery through the skin, an immediate contraction of small blood vessels, especially arteries, takes place causing a complete interruption of blood flow to said vessels. Thus, as with blood clotting, contraction of the small blood vessels prevents drugs delivered through the skin by the transdermal applicator from being delivered into the circulatory system.

Electroosmosis, which is an important factor in delivery of drugs from the applicator reservoir through the skin and into the blood circulation system, is affected by the existence of fixed negative charges on the cellular walls within the skin. A reduction of such net negative charge, as caused by passage of even small electrolytic currents or of the water ions through the skin, inhibits electroosmosis.

Blood clotting, blood vessel contraction, and reduced electroosmotic effects, as described above, can combine synergistically to slow down or completely stop transdermal delivery of primary drugs, especially from electrically powered transdermal applicators. This occurs even when the drug is successfully transferred from the applicator through the skin into the local skin tissue.

To counteract the current or drug induced loss of negative charge on the cellular walls within the skin, the electrical transdermal drug applicator with electrochemical flow enhancement, in accordance with the invention, delivers into the skin, in addition to the primary drug having therapeutic purpose, counteractive substances known to increase the negative charge on cell surfaces.

A negative charge on cell surfaces is generally accepted as a fundamental factor in preventing the clotting of blood on that surface. Negative charge (Coulombic repulsion) is also considered to be part of the mechanism for the coagulation of platelets. Additionally, overcoming negative charge is also believed to be a crucial aspect of fibrin formation, part of the avalanche of reactions in the clotting of blood (thrombosis). Without being bound by theory, for the reasons given above, it is known at a minimum, that providing a negative charge on natural or artificial surfaces in contact with animal blood helps prevent clotting or thrombosis.

One may add to the negative charge on a cell surface by reaction with or adsorption of anionic moieties compatible with animal cells such as salicylates, nitrates, methylcarboxylates, sulfonates, chlorosulfonates, phosphonates, gluconates, maleates, citrates, phthalates, or sulfates. These moieties bonded to or adsorbed on a cell surface inhibit adherence of animal blood, maintain the fluidity of animal blood, and help prevent clotting of blood in motion.

Specific drugs known as anticoagulants, antiplatelets, or antifibrotics also are negatively charged and are illustrated in the Table. Among these are heparin (a mixture containing mucosaccharide sulfonates), salicylates, protamine sulfate, potassium aminobenzoate, and nitroprusside—a source of sodium nitrate. Not only are these substances direct action drugs, they are also agents for increasing the negative charge on cell surfaces and artificial surfaces in contact with animal blood. The chemicals may be chemically bonded to, adsorbed to, or absorbed in the surface.

Another class of entities for increasing the negative charge on cell surfaces or acting to inhibit either platelet formation or coagulation of animal blood are natural substances produced by the metabolism of the animal or man Among these natural biochemical factors are: prostacyclin, thrombomodulin, Ecto-ADPase, urokinase, tissue plasminogin activators (TPA), streptokinase, antithrombin III, protein C, protein S, prostaglandins $I_2$ and $E_1$, sulfated glycosaminoglycans, N-acetylcysteine with nitroglycerin, nicoumalone, phosphatidyl inositol, hydrophilic ganglioside GM-1, cyclic GMP, S-nitrothiols, dodecapeptide gamma F1B, 400–411, and guanosine $3^1,5^1$-monophosphate, their metabolic precursors and reaction products.

Additional natural vasodilators are kinins and histamines.

Such substances, if included in the reservoir of the transdermal drug delivery applicator, move through the skin and react with the cells at the same time that the primary therapeutic drug is delivered through the skin. By maintaining a more negative condition of charge on cell surfaces, blockage of flow through local blood vessels is reduced or prevented, allowing drugs delivered transdermally to be further delivered into the systemic flow. Generally, the counteractive substance has no therapeutic value, although in special instances a substance may serve a dual purpose.

Maintaining a more negative condition of charge on cell surfaces could be achieved simultaneously and/or alternatively by precharging the cell surface with a negative charge prior to electroosmotic drug delivery in cases where such delivery takes place from the positive drug reservoir. The precharging and the discharging voltage levels are monitored and maintained within preset limits by electronic means.

In situations where one polarity of voltage delivers the primary drug and the opposite polarity delivers the counteractive substance, arrangements can be made for simultaneous delivery of both substances, or alternatively, alternating delivery can be provided.

To prevent formation of thrombi of platelets, that is, blood coagulation, adjacent the applicator/skin interface, antithrombotic agents are delivered from the applicator reservoir, either as a preconditioner or during drug delivery or alternately. Such counteractive substances would include, for example, heparin or aspirin. To counteract contraction or constriction of blood vessels adjacent the applicator interface, vasodilators can be used in the reservoir. Nitroglycerin is one such dilator. Alternatively or concomitantly, specific electrical pulses, such as square wave pulses of 0.4 ms and a frequency of 80 Hz at an intensity which could produce a tingling sensation may be used for repetitive periods of up to two hours a day to maintain vasodilation.

Accordingly, it is an object of the invention to provide an improved transdermal drug applicator and method which provide enhancement of drug flow into the system of the subject by means of delivery of counteractive agents.

Another object of the invention is to provide an improved transdermal drug applicator and method which provide, in addition to the primary therapeutic drug, a counteractor which works to make local cell charges relatively more negative.

Yet another object of the invention is to provide an improved transdermal drug applicator and method which enhance flow of primary therapeutic drug through the skin by addition of a vasodilator in the applicator reservoir.

A further object of the invention is to provide an improved transdermal drug applicator and method which provide an anticoagulant in the primary drug reservoir for delivery with the primary drug into the skin of the user.

Another object of the invention is to provide an improved transdermal drug applicator and method which captures mobile ions such as $H^+$ and $OH^-$ and thereby prevents such ions from reaching the skin tissues and causing production of thrombi, vasoconstriction and extreme changes of the cellular negative charge.

A still further object of the invention is to provide an improved transdermal drug applicator and method for the stimulation and systemic release of endogenous substances which have a natural therapeutic effect.

Still other objects and advantages of the invention will in part be obvious and will in part be apparent from the specification.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 2:
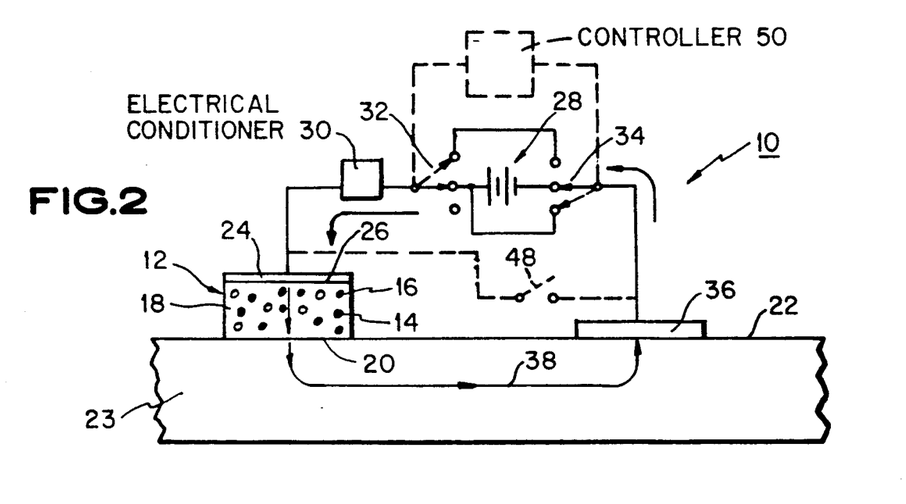
FIG. 2 is an electrical transdermal drug applicator in accordance with the invention including a single reservoir holding both a primary drug and a counteractor.

With reference to the FIG. 2, an electrical transdermal drug applicator 10 in accordance with the invention includes a reservoir 12 containing a primary drug 14 and a counteractor 16, both being dispersed in a suspension, for example, a gel 18 as disclosed in any of the above-referenced patents by the inventor here (as examples). A surface 20 of the reservoir 12 rests against the surface 22 of the user's skin 23 and is maintained in position, for example, by an adhesive (not shown). An electrode 24 connects to another surface 26 of the reservoir 12 and this in turn is connected to a DC source 28 by way of an electrical current conditioner 30 and a single pole switch 32. The other terminal of the DC source 28 connects to the skin surface 22 by way of a return electrode 36 which directly contacts the skin and is maintained in position, for example, by an adhesive (not shown). A single pole switch 34 is intermediate the electrode 36 and the DC source 28.

As discussed more fully hereinafter, the counteractor 16 acts locally on the blood vessels, for example, blood capillaries, whereas, as described in the Sibalis patents cited above, the primary drug is delivered systemically into the body's circulatory system.

Figure 1:
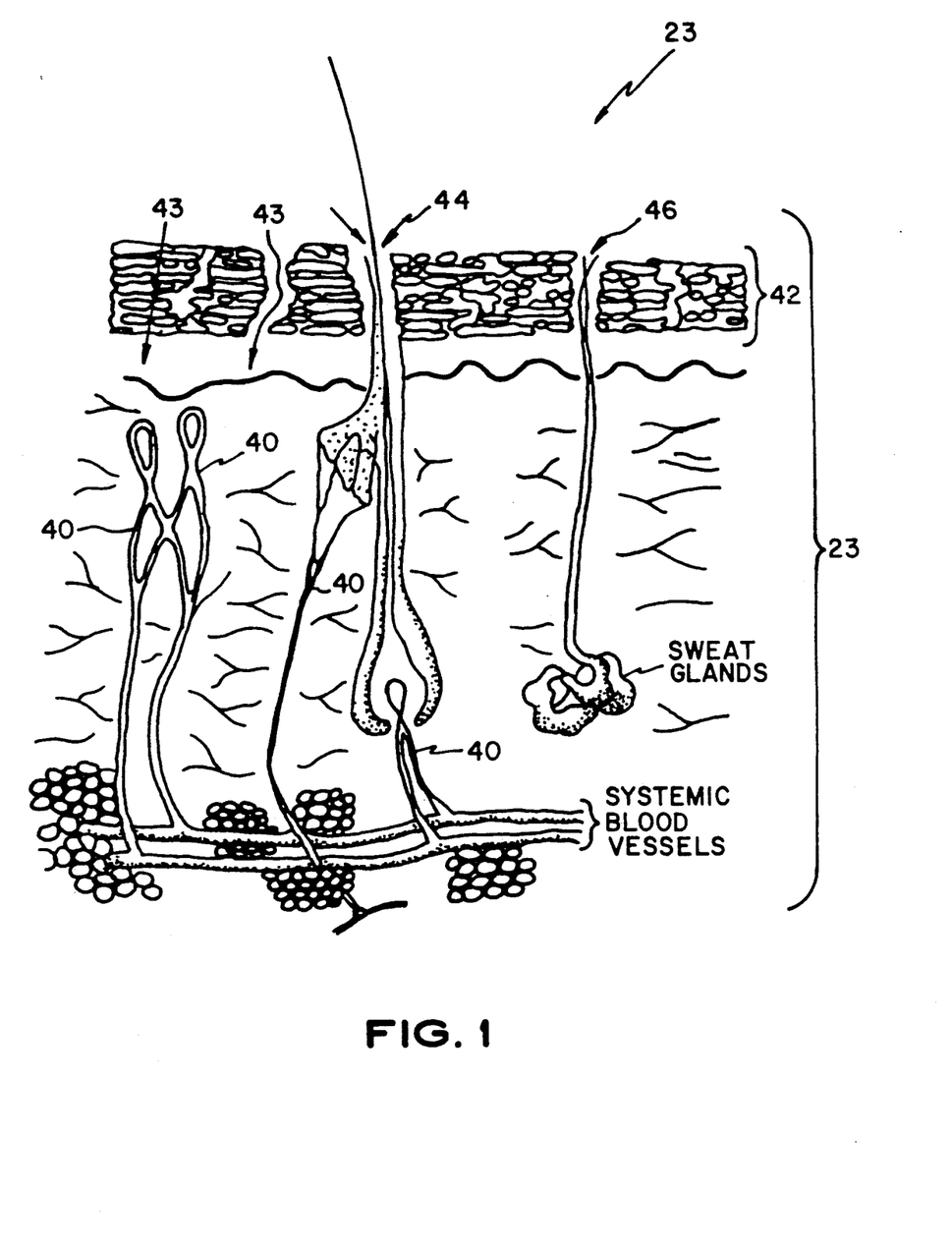
FIG. 1 is a cross-section of human skin showing pathways for transdermal drug delivery in accordance with the invention.

It should be understood that the skin 23 is illustrated in FIGS. 1, 2 with simplified representations and the electrical transdermal drug applicator is also shown schematically in FIG. 2 as a generic representation of such a device. More detailed descriptions may be found in the above-cited references by the inventor in this application. It suffices here to state that the gel 18 and the primary drug 14 and counteractor 16 are contained in the reservoir 12 in a manner to prevent leakage of the substances. Also, there is no short-circuit of electrical current across the skin surface 22 directly to the electrode 36.

When the switches 32, 34 are closed as illustrated, a positive potential appears on the electrode 24 and a negative potential on the electrode 36 causing a current to flow from the source 28 through the current conditioner 30, the electrode 24, reservoir 12 and skin surface 22 in series. A DC current flows within the skin 23 as indicated by the arrow 38, then back through the skin surface 22 to the return electrode 36, and then back through switch 34 to the negative terminal of the DC source 28. The positive potential of the source 28 applied to the electrode 24 and the electrical current drive the primary drug 14 and the counteractor 16 through the interface between the reservoir 12 and the skin surface 22.

In FIG. 1, the human skin 23 is represented in simplified construction as including an outer layer, the epidermis 42, which is broken by hair follicles 44 and sweat ducts 46, and at greater depth blood capillaries 40, glands, etc. In electrical transdermal drug applicators, it is known that small quantities of the drug pass directly through the epidermis 42 as indicated by the arrows 43 but also the drug 14 enters the skin with relative ease through the hair follicles 44 and sweat ducts 46 which act as shunts. Having entered into the skin, the drug 14 is disseminated to the systemic circulatory system by electrokinetic processes, for example, electrophoresis, electroosmosis, iontophoresis, etc. With certain drugs and counteractors it may be desirable to pick skin areas with greater or lesser densities of hair follicles and sweat ducts for application of the transdermal applicator 10 thereto.

Where a reversed polarity from that described in FIG. 2 is required to drive the primary drug 14 and counteractor 16 into the skin tissues, the switches 32, 34 in FIG. 2 are moved to the positions indicated with broken lines, whereby a negative potential is applied to the electrode 24 and a positive potential is applied to the return electrode 36.

Where the primary drug 14 and the counteractor 16 require opposite polarities of voltage to cause the substances to enter into the skin, an alternating DC potential is applied by periodically changing the positions of the switches 32, 34 such that the potentials on the electrodes 24, 36 are periodically reversed. The timing of the switches 32, 34 in each alternating position is based upon the drug 14 and counteractor 16 which are being used. Equal driving times or unequal driving times can be provided as best suited for the substances 14, 16.

Further, in recognition of the work reported by Chien et al as discussed above, it may be desirable, in the process of drug delivery, to incorporate time periods wherein no potential is applied to the electrodes 24, 36 and, it may be desirable during those periods of no driving potential, to apply a short circuit between the electrodes 24, 36 such that charges, if any, built up within the skin during the driving periods may be readily discharged. The switch 48, shown with broken lines in FIG. 2, is connected between the electrodes 24, 36 and when closed provides the desired short circuit.

In electrical transdermal drug applicators in accordance with the invention, wherein a complex operational cycle is desirable, including (for examples) polarity reversals, periods without driving potential, periods of electrode short-circuiting, etcetera, a controller 50, also shown in broken lines in FIG. 2, is used to automatically regulate opening and closing of the switches 32-35, 37, 48 in desired programs.

It should be understood that whereas the power source 28 is indicated in FIG. 2, and in the other Figures for the sake of illustration, as a DC battery, the power source may include circuitry for converting potential from a DC battery to voltages of controlled magnitude with regulated current delivery; the electrodes not being connected directly to the DC battery but to the output of the voltage generating circuitry. Additionally, the switches which are schematically represented in FIG. 2 as electro-mechanical switches can be solid state switches, especially when considering the very low current flows which are frequently involved in electrical transdermal drug applicators as indicated in the patents of the present inventor cited above. Thus complex operational cycles of an applicator in accordance with the invention may be automatically controlled by a microchip.

The counteractors 16, which are added to the reservoir 12, can operate within the skin to accomplish one or more effects which tend to maintain blood circulation in the skin area adjacent the transdermal drug applicator 10, such that the primary drug 14, which enters the skin, is carried away by the bloodstream into systemic circulation for therapeutic purposes. Broadly speaking, the counteractors 16 can include vasodilators which operate by relaxing the muscles surrounding the blood vessel walls, including capillary walls, such that a greater flow area and easier blood flow is possible. A counteractor 16 may fall in the category of antithrombosis agents in that they work to reduce platelet accumulation and blood clotting in the blood vessels, in particular the capillaries, in the area where the drug applicator 10 is applied. A single counteractor which performs both functions may be used in the reservoir 12 or a plurality of counteractors which in combination perform both functions, or a counteractor which performs only one such function may be used in the reservoir 12. Also, the counteractor 16 may be a substance which when introduced into the skin induces the body to produce substances which delay, inhibit, or eliminate blood coagulation or aid in dilating the blood vessels to improve blood circulation. The primary drug and counteractor may be variants of the same substance which do not interact pharmacologically, e.g. nitroglycerine and isosorbide dinitrate. The counteractive substance can be part of the primary drug molecule. Especially sulfonated, phospharolated and carboxylated groups attached to the primary drug molecules may be effective in providing a desired increase of the negative charge characteristics of the cellular walls where the applicator is attached.

Substances known to be unsuitable for systemic transdermal delivery as a primary drug with intended therapeutic benefit may be the preferred counteractor as the drug's action will be limited to the target area of applicator attachment and the counteractor will not be available to produce any systemic effects. Thus, such application of substances as counteractors is entirely opposed to prior teachings where it may be indicated that no therapeutic utility for these materials is present in transdermal applicators. The counteractors are formulated to function only as topical agents. For example, if nitrates are used, e.g. nitroglycerin, the flux rate of the counteractor may be adjusted so as not to produce any detectable blood serum level of the counteractor substance, while at the applicator site blood circulation is improved. There is no or negligible systemic effect or pharmacological effect. More specifically, the counteractive substance will be formulated for negligible transdermal delivery when its use is limited only to the counteractive function. The counteractive substance could be of a nature which selectively allows its delivery through the stratus corneum, such as nitroglycerin, whereas the electrokinetic main drug delivery takes place via the skin shunts, perspiration and sebaceous ducts. In such a case the stratum corneum would function as a depot for the counteractive substance even though the counteractive substance previously contained in said applicator reservoir is exhausted from the applicator.

Known vasodilators which may be used as counteractors, and known antithrombosis substances which also may be used as counteractors 16 and substances which may serve as both blood vessel dilators and also act to reduce or eliminate blood coagulation, are set forth herein below.

| TRADE NAME | GENERIC (TRIVIAL) NAME |
|---|---|
| CARDIOVASCULAR DRUGS, VASODILATORS | |
| Cerespan | papaverine hydrochloride |
| Cyclospasmol | cyclandelate |
| Ethatab | ethaverine hydrochloride |
| Lipo-Nicin | mixture of six agents: nicotinic acid, niacinamide, ascorbic acid, thiamine, HCl, riboflavin, pyridoxine |
| Pavabid | papaverine hydrochloride |
| Theo-24 | theophylline |
| Vasodilan | isoxsuprine hydrochloride |
| Cardilate | erythrityl tetranitrate |
| Iso-bid | isosorbide dinitrate |
| Isordil | isosorbide dinitrate |
| Nitro-Bid | nitroglycerine |
| Nitroglyn | nitroglycerine |
| Nitrol (ointment) | nitroglycerine (ointment) |
| Nitrospan | nitroglycerine |
| Nitrostat | nitroglycerine/polyethylene glycol |
| Peritrate | pentaerythritol tetranitrate |

-continued

| TRADE NAME | GENERIC (TRIVIAL) NAME |
|---|---|
| Persantine | dipyridamole |
| Sorbitrate | isosorbide dinitrate |
| Tridil | nitroglycerine |
| Arlidin | nylidrin hydrochloride |
| Apresoline HCl | hydralazine hydrochloride |
| Arfonad | trimethaphan camsylate |
| Dibenzyline | phenoxybenzamine hydrochloride |
| Esimil | guanethidine sulfate/hydrochloride |
| Hyperstat | diazooxide |
| Ismelin | guanethidine monosulfate |
| Loniten | minoxidil |
| Nico-400 | nitroglycerine |
| Priscoline HCl | tolazoline hydrochloride |
| Serpasil | reserpine |
| ANTICOAGULANTS | |
| Calciparine | calcium heparin |
| Coumadin | sodium warfarin (propanol-2 clathrate) |
| Heparin, Na | sodium heparin |
| Protamine sulfate | protamine sulfate |
| ANTIFIBROTICS, systemic | |
| Potaba | potassium aminobenzoate |
| ANTIPLATELET | |
| Aspirin | salicylates, such as salicylic acid, its derivatives and salts thereof. |
| OTHER | |
| | flavoroids (such as riboflavin) and their phenolic breakdown products or compounds. |
| | calcitonin gene related peptide (CGRP) |
| | nitroprusside |
| | prostacylin |
| | streptokinase |
| | urokinase |
| Activase | recombinant alteplase |

While the above listings are by no means complete, they are nevertheless representative of various categories of drugs or agents which may be suitable in the practice of the invention. Moreover, the present invention contemplates the use of any counteractors which have the specific characteristics and produce the effects desired as have been describe in the present application.

Figure 3:
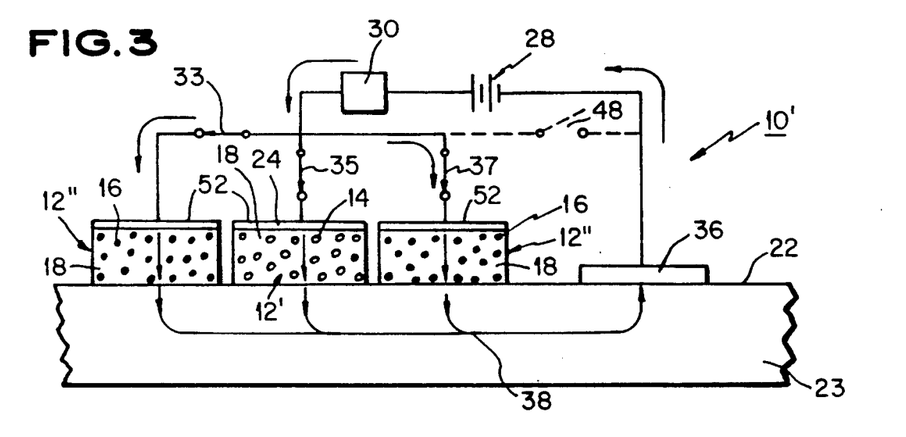
FIG. 3 is an electrical transdermal drug applicator in accordance with the invention including a parallel arrangement of reservoirs; one holding a primary drug; the others holding a counteractor.

FIG. 3 illustrates an alternative embodiment of an electrical transdermal drug applicator 10' in accordance with the invention, wherein the primary drug 14 is contained in a first reservoir 12' and the counteractor 16 is contained in the reservoirs 12". In each reservoir, the substances are suspended in a gel 18. Electrodes 24, 52 are connected in parallel to receive current from the DC power source 28 by way of the electrical current conditioner 30. As illustrated, current flows from the battery 28 through the current conditioner 30 to the electrodes 24, 52, through the associated reservoirs 12', 12", and through the surface 22 of the skin 23. The current flows (arrows 38) within the skin to the return electrode 36 and then back to the DC power source 28.

To suit a particular primary drug 14 and counteractor 16, provision for switching the polarity of the DC source 28 may be provided as indicated in FIG. 2, and a shorting circuit connecting all electrodes 24, 52 directly to the return electrode 36 by way of a switch 48 may also be included. By operation of switches 33, 35, 37, reservoirs may be selectively inactivated while the other reservoirs continue to function. A controller 50 may be used to control the switches 32, 34, 48 (see FIG. 2) when periodic cycling is involved in operation of the transdermal drug applicator 10'.

Figure 4:
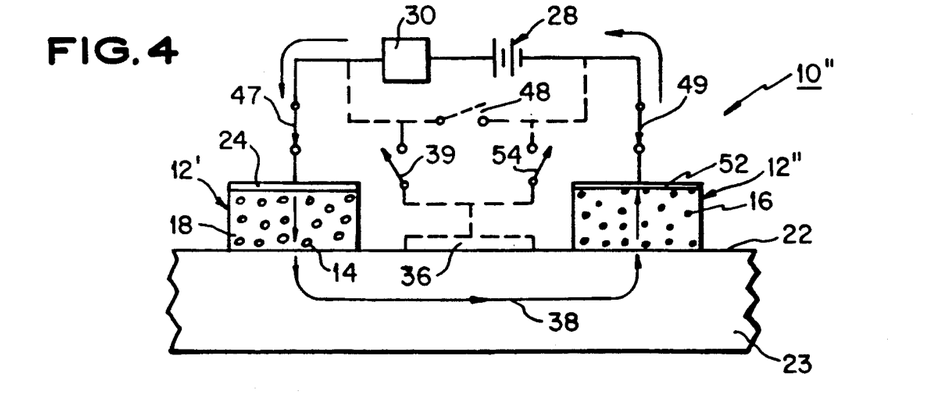
FIG. 4 is an electrical transdermal drug applicator in accordance with the invention including two reservoirs electrically in series.

FIG. 4 illustrates another alternative embodiment of an electrical transdermal drug applicator 10", In this configuration, the reservoir 12' is connected to one terminal of the DC source 28, whereas the reservoir 12" is connected to the other terminal of the DC power source 28. Thereby, opposite polarities are always present on the two reservoirs 12', 12". This is advantageous when the primary drug 14 is delivered through the skin's surface 22 by one electrical potential and the counteractor 16 is delivered through the skin surface 22 by the opposite potential. In this way, both the drug 14 and counteractor 16 can be continuously and concurrently delivered if desired.

A shorting circuit between the electrodes 24, 52 including the switch 48 may be used to remove charge, if any, from the skin during periods when the voltage is not applied. A controller 50 may be used with the configuration of FIG. 4 as described above to control ON/OFF periods, periods when the short circuit through the switch 48 is desired, etc. A return electrode 36 (broken lines) may be used to eliminate the reservoir 12' from the circuit when a switch 39 is closed while switches 47, 54 are open while switch 48 is also open. In this way, delivery of the counteractor substance 16 to the skin may continue while delivery from the reservoir 12' of the primary drug 14 is discontinued. Similarly, the return electrode 36 can be used to eliminate counteractor reservoir 12, when it is desired to deliver the drug 14 while interrupting delivery of the counteractor 16. In this case the switch 47 is closed, switches 38, 48, 49 are open and switch 54 is closed.

The electrical transdermal drug applicator 10 of FIG. 2 was described as containing a drug and a counteractor in suspension, for example, a gel. However, it should be understood that in alternative embodiments of an electrical transdermal drug applicator in accordance with the invention, the reservoir may be in the form of a matrix, liquid, paste, etc. as suits the particular substances in use. Also, FIG. 2 illustrates a generally random and equal distribution of drug 14 and counteractor 16 within the reservoir 12. It should be understood that the reservoir may contain a predominance of one substance over the other. The distribution of materials may not be uniform or randomized. The drug 14 may be in one layer, whereas a counteractor 16 may be in another layer, the layers being at different distances from the skin surface 22. As dictated by the particular application, either the drug 14 or counteractor 16 layer may be closer to the skin surface. Such layers may themselves combine several substances which can be in varying proportions as suits the particular construction with drug 14 and counteractor 16 in each layer. The layers may be of different thicknesses such that one layer may act as a flow inhibitor of materials from the other layer. There may be several layers each of counteractors and drugs and these layers may be alternated in their stacking within a reservoir.

In an exemplary embodiment of the invention, blockage of the capillaries and stratum corneum of the skin may be avoided or inhibited by sub-therapeutic dosages of an active vasodilator such as nitroglycerin. For example, a therapeutic ointment at 2% concentration is available from the W.H. Rorer Co. (Fort Washington, PA 19034) under the tradename NITROL ointment. Since it is known that nitroglycerine relaxes smooth muscles, principally in the smaller blood vessels thus dilating arterioles and capillaries, it may be advantageous to topically apply sub-therapeutic doses of about 0.001 to about 0.2% nitroglycerine ointments to the skin, when employing an otherwise conventional transdermal applicator, such as described in the applicant's own earlier issued U.S. Patents. Thus a counteractor layer is at the skin surface; the primary drug passes through this layer before entering the skin. If desired, the body of the ointment may preferably be a hydrophilic polymer, such as polyvinyl pyrrolidone or neutralized polyacrylic acid and the like in order not to interfere with the hydrophilic adhesive which may be employed in the transdermal applicator.

In another exemplary embodiment, one may utilize a stabilized vasodilator in order to restrict blockage counteraction to the region of the patient's body where the transdermal applicator of the invention is located. This may be achieved by the use of a polymer stabilizer for a vasodilator, such as nitroglycerine. One such polymer stabilizer is polyethylene glycol, but other stabilizers having like properties may also be suitable in the practice of the invention. As is known, a polyethylene glycol of molecular weight 3350 operates to lower the migration of nitroglycerine, (see U.S. Pat. No. 3,789,119). With the present invention, a higher molecular weight would be preferred, for example of from about 5000 to about 20,000 so as to localize the vasodilation of the very region where the electrolytic patch of the invention is applied. Of course, other suitable benign polymers with a molecular weight of from abut 3,000 to about 30,000 may be employed, depending on their diffusion constant.

Figure 5:
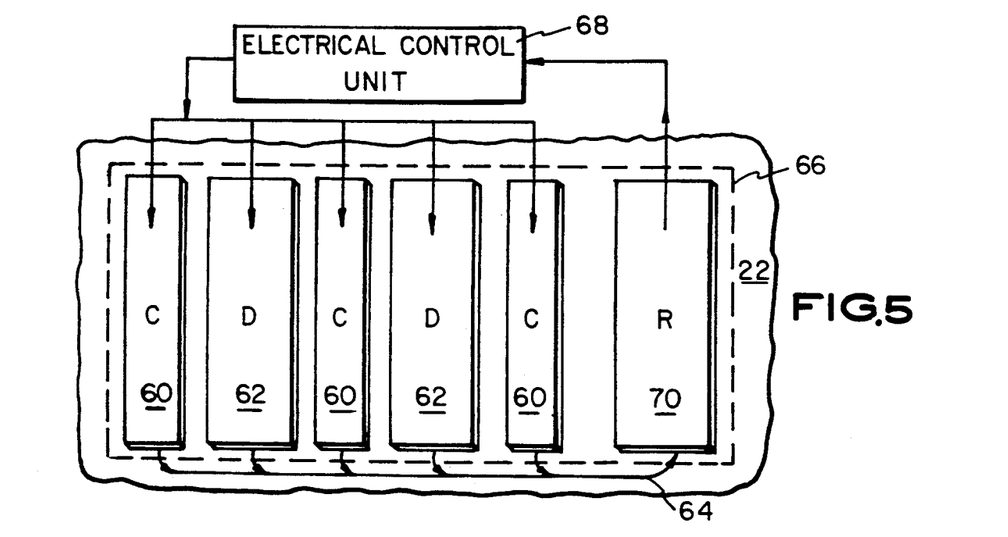
FIGS. 5-8 illustrate alternative arrangements of reservoirs and circuitry in accordance with the invention.

FIGS. 5-8 illustrate alternative embodiments in accordance with the invention wherein the primary drug indicated in those Figures with a D and the counteractive agent, indicated in those Figures with a C, are located in individual reservoirs. In FIG. 5, counteractor reservoirs 60 alternate with drug reservoirs 62 in the direction of current flow indicated by the arrows 64 when an applicator 66 is attached to the skin surface 22. For the sake of example, the reservoirs are connected in parallel schematically to one terminal of an electrical control unit 68 and current flows from the reservoirs 60, 62 through the skin surface 22 and within the skin to the return electrode 70 indicated in FIG. 5 by the letter R. The skin to which the applicator 66 is attached receives the primary drug from the reservoirs 62, while at the same time a current passing through a counteractor reservoir 60 from the upstream direction (left to right in FIG. 5) delivers the counteractive substance and acts as a preconditioner to the blood vessels in the area of the drug reservoirs 62. The counteractive substance and the primary drug are thereby simultaneously active in the same region of skin.

Figure 6:
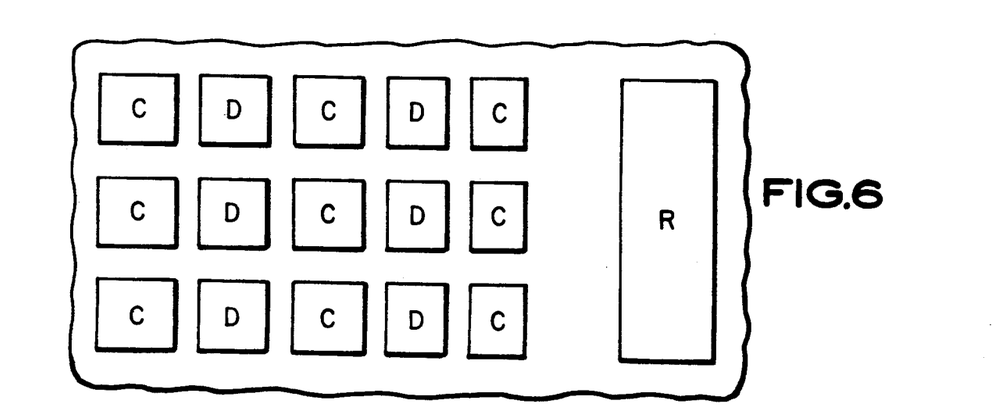
Figure 7:
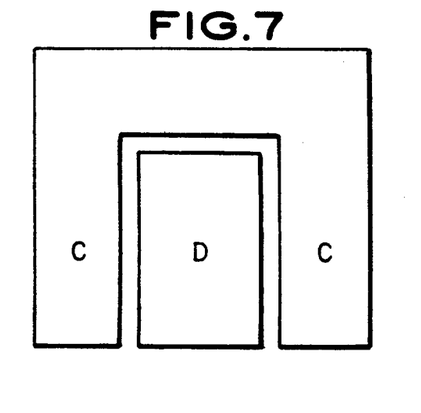
Figure 8:
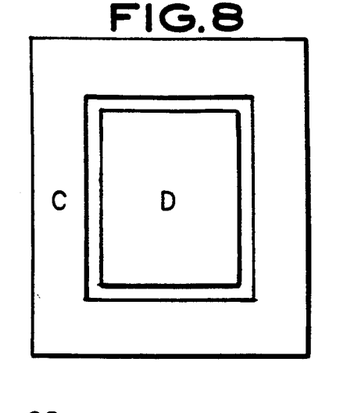

The FIGS. 5-8 are schematic. Any electrical control, such as polarity reversal, ON/OFF voltage application, electrode short-circuiting, series arrangement of reservoirs, etc., as described above in relation to FIGS. 2-4, can be applied equally to the arrangements of FIGS. 5-8. FIGS. 6, 7 and 8 show applicators with separate drug D reservoirs and counteractor C reservoirs. In each instance, the reservoirs may be electrically connected such that the counteractor substance acts as a preconditioner for the blood vessels in the area where the drug reservoir is applied. With regard to FIGS. 5-8, it should be understood that the relative positions of the primary drug reservoirs D may be interchanged with the counteractive substance reservoirs C as suits the particular substances which are in use. Other configurations as shown in the above cited patents by the inventor here, may also be adapted to utilize counteractors in conjunction with primary drug delivery.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings, shall be interpreted as illustrative and not in a limiting sense.

I claim:

1. A transdermal drug patch for delivering at least one drug to the bloodstream of a patient over an extended period of time comprising:

reservoir means for containing one or more therapeutic drugs to be applied to the bloodstream of a patient through the skin thereof, a source of DC potential having a return electrode connected to one polarity terminal thereof and said reservoir means connected to an opposite polarity terminal thereof forming an electrical series circuit when the reservoir means and return electrode are applied to the skin of the patient and interface therewith, means for operating the electrical circuit in different operational cycles to effect application of the therapeutic drug or drugs into the bloodstream of the patient through the skin by electrokinetic processes including electrophoresis and electro-osmosis in dependence upon the drug to be administered to the patient, and for at the same time electrically and electrochemically maintaining the negative surface charge density of the blood vessel walls and blood cells of the patient and effecting vasodilation of the vascular system of the patient at least in a region where the transdermal patch is attached to the skin of the patient.

2. A transdermal drug patch for delivering at least one drug to the bloodstream of a patient over an extended period of time according to claim 1, in which the reservoir means contains a vasodilator in addition to one or more therapeutic drugs.

3. A transdermal drug patch for delivering at least one drug to the bloodstream of a patient over an extended period of time according to claim 1, in which said means for operating the electrical circuit in different operational cycles comprises an electrical current conditioner connected between said source and said reservoir means in series therewith.

4. A transdermal drug patch for delivering at least one drug to the bloodstream of a patient over an extended period of time according to claim 1, in which said means for operating the electrical circuit in different operational cycles comprises switching means for effecting polarity reversals.

5. A transdermal drug patch for delivering at least one drug to the bloodstream of a patient over an extended period of time according to claim 1, in which said means for operating the electrical circuit in different operational cycles comprises means for varying periods in which the circuit is free of electrical potential during an operational cycle.

6. A transdermal drug patch for delivering at least one drug to the bloodstream of a patient over an extended period of time according to claim 1, in which said means for operating the electrical circuit in different operational cycles comprises means for selectively effecting a short circuit between said reservoir means and said return electrode.

7. A transdermal drug patch for delivering at least one drug to the bloodstream of a patient over an extended period of time in accordance with claim 1, in which said reservoir means contains a substance for delivery to the bloodstream of the patient for effecting said vasodilation.

* * * * *